(12) United States Patent
Ren et al.

(10) Patent No.: US 12,378,252 B2
(45) Date of Patent: Aug. 5, 2025

(54) PYRROLOPYRAZOLE DERIVATIVES, PREPARATION METHOD THEREOF AND APPLICATION THEREOF IN MEDICINE

(71) Applicants: SHANGHAI MEDICILON INC., Shanghai (CN); MEDICILON PRECLINICAL RESEARCH (SHANGHAI) LLC., Shanghai (CN)

(72) Inventors: Feng Ren, Shanghai (CN); Yongmei Xu, Shanghai (CN); Xianlian Wang, Shanghai (CN); Chunlin Chen, Shanghai (CN); Jinna Cai, Shanghai (CN)

(73) Assignees: SHANGHAI MEDICILON INC., Shanghai (CN); MEDICILON PRECLINICAL RESEARCH (SHANGHAI) LLC., Shanghai (CN)

( * ) Notice: Subject to any disclaimer, the term of this patent is extended or adjusted under 35 U.S.C. 154(b) by 863 days.

(21) Appl. No.: 17/630,124

(22) PCT Filed: Aug. 26, 2019

(86) PCT No.: PCT/CN2019/102524
§ 371 (c)(1),
(2) Date: Jan. 25, 2022

(87) PCT Pub. No.: WO2021/017066
PCT Pub. Date: Feb. 4, 2021

(65) Prior Publication Data
US 2022/0267336 A1   Aug. 25, 2022

(30) Foreign Application Priority Data

Jul. 26, 2019 (CN) .......................... 201910683537.5

(51) Int. Cl.
*C07D 487/04* (2006.01)
(52) U.S. Cl.
CPC .................................. *C07D 487/04* (2013.01)
(58) Field of Classification Search
None
See application file for complete search history.

(56) References Cited

FOREIGN PATENT DOCUMENTS

WO    WO 2005/040169 A2 *  5/2005  ........... C07D 487/00

* cited by examiner

*Primary Examiner* — Brian J Davis
(74) *Attorney, Agent, or Firm* — Alleman Hall & Tuttle LLP

(57) ABSTRACT

Disclosed are a pyrrolopyrazole derivative, a preparation method therefor, and the medical use thereof. In particular, disclosed are a novel class of pyrrolopyrazole derivatives represented by general formula (I), a preparation method therefor, and the use of the pyrrolopyrazole derivatives or pharmaceutical compositions containing the pyrrolopyrazole derivatives in biomedicine as therapeutic agents, particularly as gastric acid secretion inhibitors and potassium ion competitive acid blockers (P-CABs). The definitions of various substituent ($R^1$, $R^2$, $R^3$, $R^4$) and the group (X) in general formula (I) are the same as the definitions in the description.

3 Claims, No Drawings

PYRROLOPYRAZOLE DERIVATIVES, PREPARATION METHOD THEREOF AND APPLICATION THEREOF IN MEDICINE

TECHNICAL FIELD

The present invention relates to a novel class of pyrrolopyrazole derivatives, to a process for their preparation, and to their use as therapeutic agents, especially as inhibitors of gastric acid secretion and as competitive acid blockers (P-CABs) of potassium ion, or pharmaceutical compositions containing them.

BACKGROUND

Peptic ulcer mainly refers to chronic ulcer that occurs in stomach and duodenum. Although there are regional differences, the incidence of peptic ulcer usually accounts for 10% to 20% of the total population, and is a frequently-occurring disease or a common disease. Ulcer formation is due to various factors, and the digestion of the mucosa by acidic gastric juice is the essential factor in ulcer formation. Therefore, inhibition of gastric acid secretion is becoming the first method for the treatment of peptic ulcer diseases.

Since the first Proton Pump Inhibitors (PPIs) omeprazole was marketed in 1988, several products of PPIs have been marketed globally to date, including lansoprazole, pantoprazole, rabeprazole, and esomeprazole. PPIs have become the first choice drugs for the treatment of gastric acid-related diseases, including peptic ulcer, reflux esophagitis and Zollinger-Ehrlich syndrome. The Proton Pump is essentially $H^+/K^+$-adenosine triphosphatase ($H^+/K^+$-ATPase), which specifically pumps protons ($H^+$) into the stomach cavity to form a strong acid in the stomach. Proton Pump inhibitors can inhibit the activity of the proton pump and thereby regulate the secretion of gastric acid mediated by the proton pump.

Potassium-Competitive Acid Blockers (P-CABs) are a novel class of gastric acid blockers thus play a role in inhibiting the enzyme activity of $H^+/K^+$-ATPase by reversibly binding $H^+/K^+$-ATPase competitively with potassium ions ($K^+$). Compared with PPIs, the P-CABs have the characteristics of lipophilicity, alkalescence, stability under acidic (low pH) conditions and the like. At the same time, the P-CABs have the advantages of quick response, easier achievement of acid inhibition effect and the like.

The first new P-CABs drug Voronolazan was marketed in Japan in 2014 for the treatment of gastric acid-related diseases such as peptic ulcer. A series of the structures of potassium ion-competitive acid blockers have also been disclosed. However, there is still a need to develop new compounds with diversified structural types and better medicinal properties.

SUMMARY

In view of the above-mentioned problems, the object of the present invention is to provide a compound for treating gastric acid-related diseases such as peptic ulcer, which is of a novel structural type and has excellent effects and actions.

In a first aspect, the present invention provides a compound represented by general formula (I) or a pharmaceutically acceptable salt thereof,

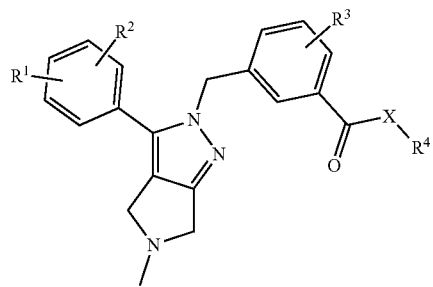

Wherein:
X is selected from O or $NR^a$, wherein $R^a$ is selected from hydrogen atom or alkyl;
$R^1$ and $R^2$ are each independently selected from hydrogen atom, halogen or alkyl;
$R^3$ is selected from hydrogen atom, halogen, hydroxyl or alkane;
$R^4$ is selected from alkyl, $C_{3-6}$ cycloalkyl, $C_{1-4}$ alkyl amide.
Preferably, X is selected from O or NH;
$R^1$ and $R^2$ are each independently selected from hydrogen atom, halogen or $C_{1-3}$ alkyl group;
$R^3$ is selected from hydrogen atom or a halogen;
$R^4$ is selected from $C_{1-4}$ alkyl group, $C_{3-5}$ cycloalkyl group, and $C_{1-4}$ alkyl amide.
Preferably, X is selected from O or NH;
$R^1$ and $R^2$ are each independently selected from hydrogen atom, fluorine atom or methyl;
$R^3$ is selected from hydrogen atom or fluorine atom; $R^4$ is selected from methyl, ethyl, n-butyl, tert-butyl, cyclopropyl, $C_{1-4}$ alkyl amide.
Preferably, the compound is selected from:
3-((3-(2-fluorophenyl)-5-methyl-5,6-dihydropyrrolo[3,4-c]pyrazole-2(4H)-yl)methyl)benzoic acid ester;
3-((3-(2-fluorophenyl)-5-methyl-5,6-dihydropyrrolo[3,4-c]pyrazole-2(4H)-yl)methyl)butyl benzoate ester;
3-((3-(2-fluorophenyl)-5-methyl-5,6-dihydropyrrolo[3,4-c]pyrazole-2(4H)-yl)methyl)ethyl benzoate;
N-cyclopropyl-3-((3-(2-fluorophenyl)-5-methyl-5,6-dihydropyrrolo[3,4-c]pyrazole-2(4H)-yl)methyl)benzamide;
1-amino-2-methyl-1-oxoprop-2-yl-3-((3-(2-fluorophenyl)-5-methyl-5,6-dihydropyrrolo[3,4-c)pyrazole-2(4H)-yl)methyl)benzoate;
3-((5-methyl-3-(o-tolyl)-5,6-dihydropyrrolo[3,4-c]pyrazole-2(4H)-yl)methyl)benzoate;
2-fluoro-5-((5-methyl-3-(o-tolyl)-5,6-dihydropyrrole[3,4-c]pyrazole-2(4H)-yl)methyl)benzoic acid methyl ester;
3-((5-methyl-3-(o-tolyl)-5,6-dihydropyrrolo[3,4-c]pyrazole-2(4H)-yl)methyl)benzoate;
3-((3-(2,4-difluorophenyl)-5-methyl-5,6-dihydropyrrolo[3,4-c]pyrazole-2(4H)-yl) methyl) methyl benzoate.

In a second aspect, the present invention provides a pharmaceutical composition, comprising the compound represented by general formula (I) or a pharmaceutically acceptable salt thereof and a pharmaceutically acceptable carrier, excipient, or diluent.

In a third aspect, the present invention provides an application of the compound represented by general formula (I) or the pharmaceutically acceptable salt thereof, and the above-mentioned pharmaceutical composition in preparing a gastric acid secretion inhibitor.

In a fourth aspect, the present invention provides an application of the compound represented by general formula (I) or the pharmaceutically acceptable salt thereof, and the above-mentioned pharmaceutical composition in preparing an H+/K+-adenosine triphosphatase inhibitor.

In a fifth aspect, the present invention provides an application of the compound represented by general formula (I) or the pharmaceutically acceptable salt thereof, and the above-mentioned pharmaceutical composition in preparing a potassium ion competitive acid blocker.

In a sixth aspect, the present invention provides an application of the compound represented by general formula (I) or the pharmaceutically acceptable salt thereof, and the above-mentioned pharmaceutical composition in preparing a medicament for the treatment and/or prevention of peptic ulcer, Zollinger-Ellison Syndrome, gastritis, erosive esophagitis, reflux esophagitis, symptomatic gastroesophageal reflux disease, Barrett's esophagitis, functional dyspepsia, *Helicobacter pylori* infection, gastric cancer, gastric MALT lymphoma, ulcers caused by non-steroidal anti-inflammatory drugs, or hyperacidity or ulcers caused by post-operative stress; or inhibiting peptic ulcer, acute stress ulcer, hemorrhagic gastritis, or upper gastrointestinal bleeding caused by invasive stress.

DETAILED DESCRIPTION

The present invention will be further described below through the following embodiments. It should be understood that the following embodiments are only used to illustrate the present invention, not to limit the present invention.

Unless stated to the contrary, the following terms used in the specification and claims have the following meanings.

The term "alkyl" refers to a saturated aliphatic hydrocarbon group, including straight or branched chain groups of 1 to 10 carbon atoms. Preferably, an alkyl groups containing 1 to 5 carbon atoms. More preferably, an alkyl group containing 1 to 3 carbon atoms, such as methyl, ethyl, n-propyl, isopropyl.

The carbon atom content of various hydrocarbon containing moieties is indicated by the prefix designating the minimum and maximum number of carbon atoms for that moiety, i.e., the prefixes $C_{i-j}$ indicate that the number of carbon atoms for that moiety ranges from integers "i" to integers "j" (including i and j). Thus, for example, $C_{1-3}$ alkyl refers to alkyl groups of 1 to 3 carbon atoms (including 1 and 3).

The term "hydroxy" refers to an —OH group.

The term "halogen" refers to fluorine, chlorine, bromine or iodine.

Unless otherwise specified, all occurrences of the compounds herein are intended to comprise all possible isomers, such as tautomers, enantiomers, diastereomers, and mixtures thereof.

The term "compound of the present invention" refers to a compound represented by the general formula (I). The term also comprises various crystalline forms of the compound of general formula (I), pharmaceutically acceptable salts, hydrates or solvates.

The term "pharmaceutically acceptable salt" refers to salts formed by the compounds of the present invention with acids or bases that are suitable for use as pharmaceutical agents. Pharmaceutically acceptable salts include inorganic salts and organic salts. One preferred class of salts is that formed from the compounds of the present invention and acids. Suitable acids for forming salt include, but are not limited to: inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid, benzenesulfonic acid, etc.; and acidic amino acids such as aspartic acid and glutamic acid.

The term "pharmaceutically acceptable carrier" refers to a carrier that can be used in the preparation of pharmaceutical compositions, which are generally safe, non-toxic, not biologically or otherwise undesirable, and comprises carriers that are pharmaceutically acceptable by animals and humans. As used in the specification and claims, a "pharmaceutically acceptable carrier" comprises one or more such carriers.

The terms "comprise", "contain" or "include" mean that the various ingredients may be used together in a mixture or composition of the present invention. Therefore, the terms "mainly consist of" and "consist of" are encompassed by the term "comprise".

The term "prevention" refers, for example, to the prevention of development of clinical symptoms of a disease in a mammal that may be exposed to or predisposed to the disease but has not yet experienced or displayed symptoms of the disease.

The term "treatment" may refer to inhibiting a disease, such as preventing or reducing the development of a disease or clinical symptoms thereof, or relieving a disease, such as causing regression of a disease or clinical symptoms thereof.

Compound of general formula (I)

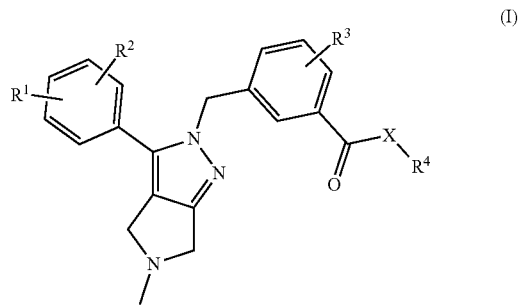

In some embodiments of the present invention, X is selected from O or $NR^a$, wherein $R^a$ is selected from hydrogen atom or alkyl. In a more preferred embodiment, X is selected from O or NH.

In some embodiments of the present invention, $R^1$ and $R^2$ are each independently selected from hydrogen atom, halogen, or alkyl. In a more preferred embodiment, $R^1$ and $R^2$ are each independently selected from hydrogen atom, halogen, or $C_{1-3}$ alkyl group. In a further preferred embodiment, $R^1$ and $R^2$ are each independently selected from hydrogen atom, fluorine atom, or methyl.

In some embodiments of the present invention, at least one of $R^1$ and $R^2$ is not hydrogen atom. In some embodiments of the present invention, at least one of $R^1$ and $R^2$ is in the position of 2. In some embodiments of the present invention, $R^1$ and $R^2$ are respectively located at positions of 2 and 4.

In some embodiments of the present invention, $R^3$ is selected from hydrogen atom, halogen, hydroxyl, or alkyl. In a more preferred embodiment, $R^3$ is selected from hydrogen atom or halogen. In a further preferred embodiment, $R^3$ is selected from hydrogen atom or fluorine atom.

In some embodiments of the present invention, $R^3$ may be in the ortho position to the carbonyl group on the phenyl ring.

In some embodiments of the present invention, $R^4$ is selected from alkyl, $C_{3-6}$ cycloalkyl groups, and $C_{1-4}$ alkyl amides. In a more preferred embodiment, $R^4$ is selected from $C_{1-4}$ alkyl groups, $C_{3-5}$ cycloalkyl groups, and $C_{1-4}$ alkyl amides. In a further preferred embodiment, $R^4$ is selected from methyl, ethyl, n-butyl, tert-butyl, cyclopropyl, $C_{1-4}$ alkyl amide.

The $C_{1-4}$ alkyl amide means that one hydrogen atom on the $C_{1-4}$ alkyl group is replaced by —C(=O)NH2. When $R^4$ is a $C_{1-4}$ alkyl amide, the compound of formula (I) can be represented by the following formula:

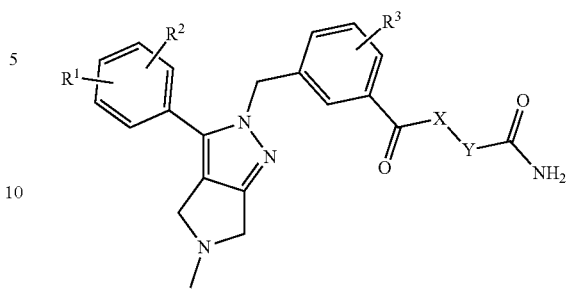

(II)

Wherein, Y is $C_{1-4}$ alkylene group. The term "alkylene" refers to a divalent alkyl group.

In some embodiments of the present invention, the compound of general formula (I) is selected from the compounds shown in Table 1.

TABLE 1

| Compound number | Compound structure | Compound naming |
|---|---|---|
| 1 | 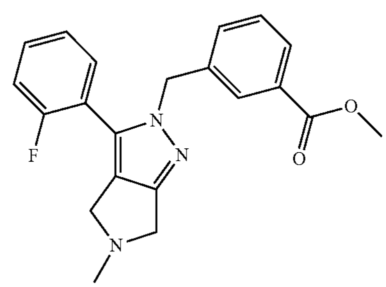 | 3-((3-(2-fluorophenyl)-5-methyl-5,6-dihydropyrrolo[3,4-c]pyrazole-2(4H)-yl)methyl)benzoic acid ester; |
| 2 | 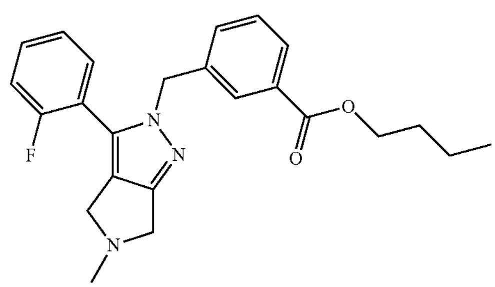 [SMILES: CCCCOC(=O)c1cccc(Cn2nc3c(c2-c2ccccc2F)CN(C)C3)c1] | 3-((3-(2-fluorophenyl)-5-methyl-5,6-dihydropyrrolo[3,4-c]pyrazole-2(4H)-yl)methyl)butyl benzoate ester; |
| 3 | 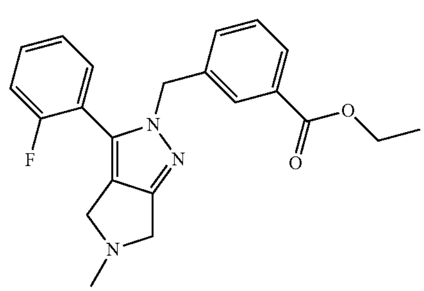 [SMILES: CCOC(=O)c1cccc(Cn2nc3c(c2-c2ccccc2F)CN(C)C3)c1] | 3-((3-(2-fluorophenyl)-5-methyl-5,6-dihydropyrrolo[3,4-c]pyrazole-2(4H)-yl)methyl)ethyl benzoate; |

TABLE 1-continued

| Compound number | Compound structure | Compound naming |
|---|---|---|
| 4 | 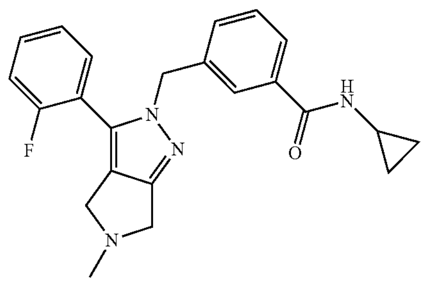 [SMILES: CN1Cc2nn(Cc3cccc(C(=O)NC4CC4)c3)c(-c3ccccc3F)c2C1] | N-cyclopropyl-3-((3-(2-fluorophenyl)-5-methyl-5,6-dihydropyrrolo[3,4-c]pyrazole-2(4H)-yl)methyl)benzamide; |
| 5 | 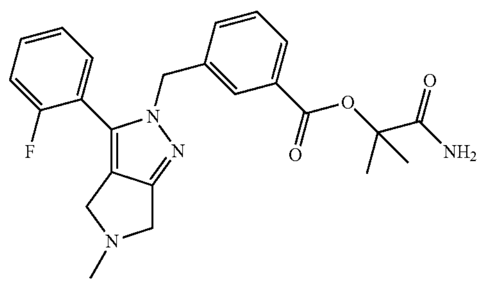 [SMILES: CN1Cc2nn(Cc3cccc(C(=O)OC(C)(C)C(N)=O)c3)c(-c3ccccc3F)c2C1] | 1-amino-2-methyl-1-oxoprop-2-yl-3-((3-(2-fluorophenyl)-5-methyl-5,6-dihydropyrrolo[3,4-c]pyrazole-2(4H)-yl)methyl)benzoate; |
| 6 | 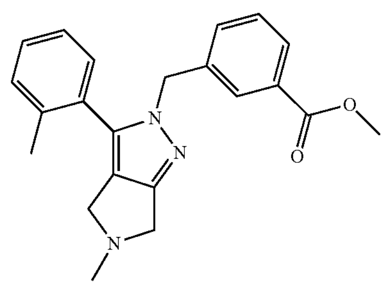 [SMILES: COC(=O)c1cccc(Cn2nc3c(c2-c2ccccc2C)CN(C)C3)c1] | 3-((5-methyl-3-(o-tolyl)-5,6-dihydropyrrolo[3,4-c]pyrazole-2(4H)-yl)methyl)benzoate; |
| 7 | 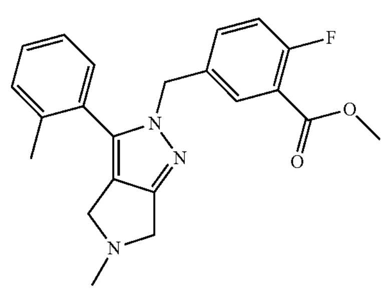 [SMILES: COC(=O)c1cc(Cn2nc3c(c2-c2ccccc2C)CN(C)C3)ccc1F] | 2-fluoro-5-((5-methyl-3-(o-tolyl)-5,6-dihydropyrrole[3,4-c]pyrazole-2(4H)-yl)methyl)benzoic acid methyl ester; |
| 8 | 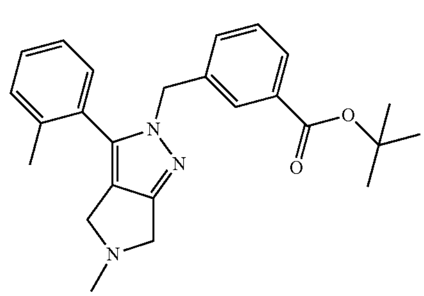 [SMILES: Cc1ccccc1-c1c2c(nn1Cc1cccc(C(=O)OC(C)(C)C)c1)CN(C)C2] | 3-((5-methyl-3-(o-tolyl)-5,6-dihydropyrrolo[3,4-c]pyrazole-2(4H)-yl)methyl)benzoate; |

TABLE 1-continued

| Compound number | Compound structure | Compound naming |
|---|---|---|
| 9 | 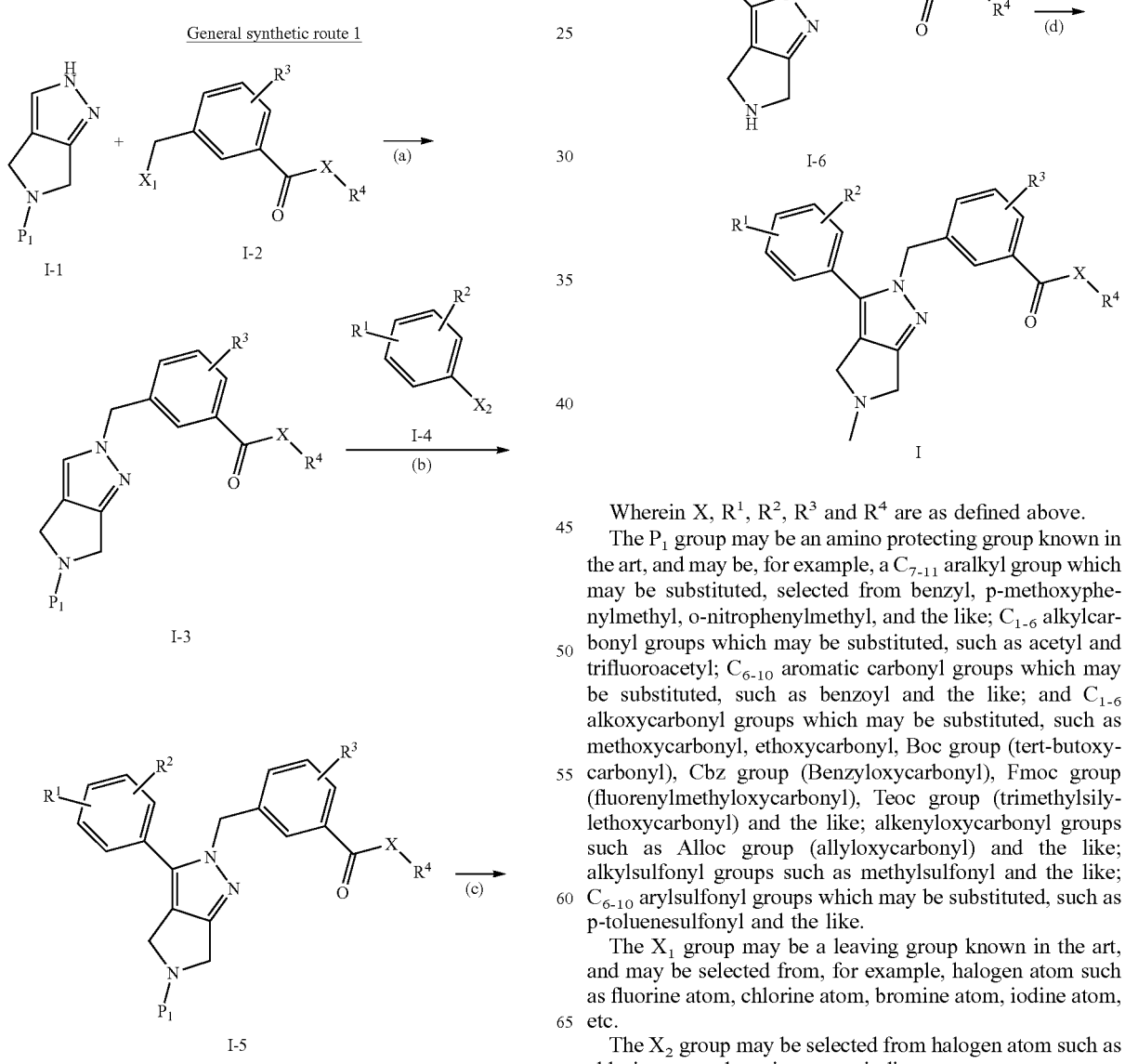 | 3-((3-(2,4-difluorophenyl)-5-methyl-5,6-dihydropyrrolo[3,4-c]pyrazole-2(4H)-yl)methyl)methyl benzoate. |

Preparation method of compound of general formula (I)

In some embodiments of the present invention, the compounds of general formula (I) may be prepared using the following general synthetic route 1:

Wherein X, $R^1$, $R^2$, $R^3$ and $R^4$ are as defined above.

The $P_1$ group may be an amino protecting group known in the art, and may be, for example, a $C_{7-11}$ aralkyl group which may be substituted, selected from benzyl, p-methoxyphenylmethyl, o-nitrophenylmethyl, and the like; $C_{1-6}$ alkylcarbonyl groups which may be substituted, such as acetyl and trifluoroacetyl; $C_{6-10}$ aromatic carbonyl groups which may be substituted, such as benzoyl and the like; and $C_{1-6}$ alkoxycarbonyl groups which may be substituted, such as methoxycarbonyl, ethoxycarbonyl, Boc group (tert-butoxycarbonyl), Cbz group (Benzyloxycarbonyl), Fmoc group (fluorenylmethyloxycarbonyl), Teoc group (trimethylsilylethoxycarbonyl) and the like; alkenyloxycarbonyl groups such as Alloc group (allyloxycarbonyl) and the like; alkylsulfonyl groups such as methylsulfonyl and the like; $C_{6-10}$ arylsulfonyl groups which may be substituted, such as p-toluenesulfonyl and the like.

The $X_1$ group may be a leaving group known in the art, and may be selected from, for example, halogen atom such as fluorine atom, chlorine atom, bromine atom, iodine atom, etc.

The $X_2$ group may be selected from halogen atom such as chlorine atom, bromine atom, iodine atom, etc.

In step (a), the compound of formula I-1 is reacted with the compound of formula I-2 to obtain the compound of formula I-3.

The molar ratio of the compound of formula I-1 to the compound of formula I-2 can be 1:(0.5 to 3.0). The reaction solvent may be acetonitrile, acetone, tetrahydrofuran, dioxane, N,N-dimethylformamide, etc. The reaction of step (a) may be carried out in the presence of a base. The base can be selected from: cesium carbonate, potassium carbonate, sodium carbonate, potassium hydroxide, sodium hydroxide, and the like. The molar ratio of the compound of formula I-1 to the base can be 1:(1.0 to 6.0). The reaction temperature of step (a) may be appropriately set by those skilled in the art, and may be, for example, 0 to 100° C.

In step (b), the compound of formula I-3 is reacted with the compound of formula I-4 to obtain the compound of formula I-5.

The molar ratio of the compound of formula I-3 to the compound of formula I-4 can be 1:(0.5 to 3.0). The reaction solvent may be acetonitrile, acetone, tetrahydrofuran, dioxane, N,N-dimethylformamide, etc. Step (b) may be carried out in the presence of a palladium catalyst. The palladium catalyst can be selected from: allylpalladium(II) chloride dimer, tris(dibenzylideneacetone)dipalladium, [1,1'-bis(diphenylphosphino)ferrocene] Palladium dichloride, palladium chloride, and the like. Alternatively, the reaction of step (b) may be carried out in the presence of a base. The base may be selected from: potassium acetate, sodium acetate, potassium phosphate, potassium dihydrogen phosphate, potassium bistrimethylsilylamine, sodium bistrimethylsilylamine, and the like. The molar ratio of the compound of formula I-3 to the base can be 1:(0.5 to 3.0). The reaction temperature in step (b) may be appropriately set by those skilled in the art, and may be, for example, 40 to 150° C.

In step (c), the $P_1$ protecting group is removed. The reaction conditions may be those commonly used in the art for deprotecting an amino protecting group. For example, when P1 is Boc, it can be treated with a protic acid (for example, trifluoroacetic acid) or a Lewis acid.

In step (d), the compound of formula I-6 is subjected to an aminomethylation reaction to obtain the compound of formula I. This step may employ aminomethylation reaction conditions well known in the art. In some embodiments, the compound of formula I-6 is stirred with formaldehyde for a period of time to generate a Schiff base, and then reacted with a reducing agent such as sodium borohydride acetate, for a period of time to obtain the compound of formula I.

In some embodiments of the present invention, the following general synthetic route 2 can be used to prepare the compounds of general formula (I):

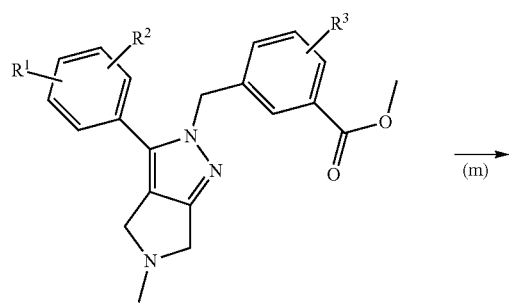

I-8

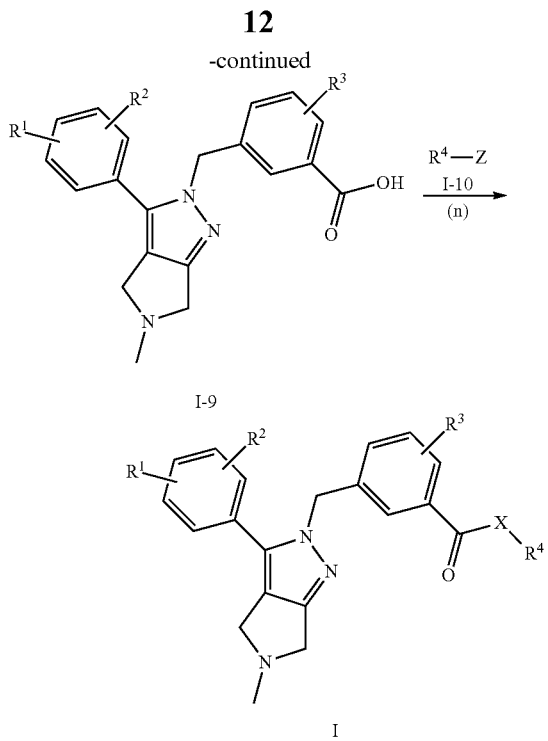

Wherein the definitions of X, $R^1$, $R^2$, $R^3$, $R^4$ are as described above.

The compounds of formula I-8 may be obtained by the general synthetic route 1 described above.

In step (m), the compounds of formula I-8 are hydrolyzed to obtain the compounds of formula I-9. The reaction may be carried out under alkaline conditions, and the base used may be selected from, for example, lithium hydroxide, sodium hydroxide, and potassium hydroxide.

In step (n), the compounds of formula I-9 are reacted with the compounds of formula I-10 to obtain the compounds of formula I.

In the compounds of formula I-10, Z may be hydroxy, amino, halogen and the like. When Z is hydroxyl, the reaction may be carried out under acidic conditions such as the presence of concentrated sulfuric acid. When Z is amino, the reaction may be carried out in the presence of condensing agents. The condensing agents may be selected from HATU, EDCI, and CDI, for example, when Z is halogen such as Br, the reaction may be carried out under alkaline conditions or in the presence of silver oxide.

Application of the compounds of general formula (I)

The compounds of general formula (I) can be used as inhibitors of gastric acid secretion.

The compounds of general formula (I) can be used as $H/K^+$-ATPase inhibitors.

The compounds of general formula (I) can be used as potassium ion competitive acid blockers (P-CABs).

The compounds of general formula (I) can be used for treating and/or preventing peptic ulcer, Zollinger-Ehrlich syndrome, gastritis, erosive esophagitis, reflux esophagitis, symptomatic gastroesophageal reflux disease, Barrett's esophagitis, functional dyspepsia, *Helicobacter pylori* infection, gastric cancer, gastric MALT lymphoma, ulcers caused by non-steroidal anti-inflammatory drugs, or hyperacidity or ulcers caused by post-operative stress; or inhibiting peptic ulcers, acute stress ulcers, Haemorrhagic gastritis or upper gastrointestinal bleeding caused by invasive stress. The aforementioned peptic ulcer includes but is not limited to gastric ulcer, duodenal ulcer or anastomotic ulcer. Symptomatic gastroesophageal reflux disease includes but is not limited to non-erosive reflux disease or gastroesophageal reflux disease without esophagitis.

Pharmaceutical Composition

The pharmaceutical composition of the present invention comprises an effective amount of the compound represented by the general formula (I) or tautomer, enantiomer, diastereomer, and mixture form thereof, pharmaceutically acceptable salt thereof, and pharmaceutically acceptable carrier or excipient or diluent.

"Effective amount" means the compound of the present invention: (i) treating a particular disease, condition or disorder, (ii) attenuating, ameliorating or eliminating one or more symptoms of a particular disease, condition or disorder, or (iii) preventing or delaying the onset of one or more symptoms of a particular disease, condition, or disorder described herein.

Examples of pharmaceutically acceptable carriers moieties are cellulose and its derivatives (e.g., sodium carboxymethyl cellulose, sodium ethyl cellulose, cellulose acetate, etc.), gelatin, talc, and solid lubricants (e.g., stearic acid, magnesium stearate), calcium sulfate, vegetable oils (e.g., soybean oil, sesame oil, peanut oil, olive oil, etc.), polyols (e.g., propylene glycol, glycerin, mannitol, sorbitol, etc), emulsifiers (e.g., Tween), wetting agents (e.g., sodium lauryl sulfate), colorants, flavors, stabilizers, antioxidants, preservatives, pyrogen-free water, and the like.

The mode of administration of the compounds or pharmaceutical compositions of the present invention is not particularly limited, and representative modes of administration include (but are not limited to): oral, intratumoral, rectal, parenteral (intravenous, intramuscular, or subcutaneous), and topical administration.

The compounds of the present invention may be administered alone or in combination with other pharmaceutically acceptable compounds.

Another aspect of the present invention relates to a method of inhibiting the secretion of gastric acid, which comprises administering to a patient in need of an effective amount of the compound represented by the general formula (I) or its tautomers, enantiomers, and diastereomers, and mixtures thereof, and pharmaceutically acceptable salts or pharmaceutical compositions thereof.

Another aspect of the present invention relates to a method for inhibiting $H^+/K^+$-adenosine triphosphatase ($H^+/K^+$-ATPase) comprising administering to a patient in need of an effective amount of the compound of formula (I) or its tautomers, enantiomers, diastereomers, and mixtures thereof, and pharmaceutically acceptable salts thereof or pharmaceutical compositions thereof.

Hereinafter, the present invention will be further described with the following examples. It should be understood that the following examples are used to explain this invention and do not mean to limit the scope of this invention. Any non-essential improvements and modifications made by a person skilled in the art based on this invention all fall into the protection scope of this invention. The specific process parameters below are only exemplary, and a person skilled in the art can choose proper values within an appropriate range according to the description, and are not restricted to the specific values shown below.

The structure of the compound is determined by nuclear magnetic resonance (NMR) or mass spectrometry (MS), and the purity of the compound is determined by liquid high pressure chromatography (HPLC). NMR was measured using a Bruker AVANCE-400 nuclear magnetic resonance apparatus in deuterated dimethyl sulfoxide (DMSO-d6) or deuterated methanol (MeOH-d4) as the solvent and tetramethylsilane (TMS) as the internal standard and chemical shifts in ppm. MS was determined using an Agilent 6120 mass spectrometer. HPLC was measured using an Agilent 1200DAD high pressure liquid chromatograph.

Example 1

3-((3-(2-fluorophenyl)-5-methyl-5,6-dihydropyrrolo[3,4-c]pyrazole-2(4H)-yl)methyl)benzoic acid ester

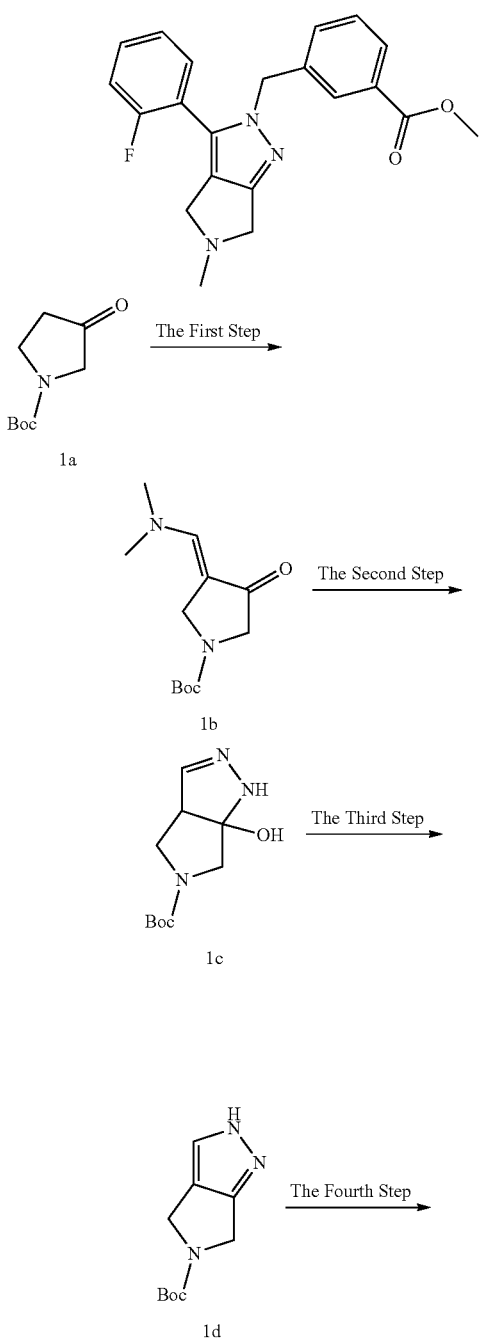

The First Step tert-butyl (E)-3-((dimethylamino)methylene)-4-oxopyrrolidine-1-carboxylate

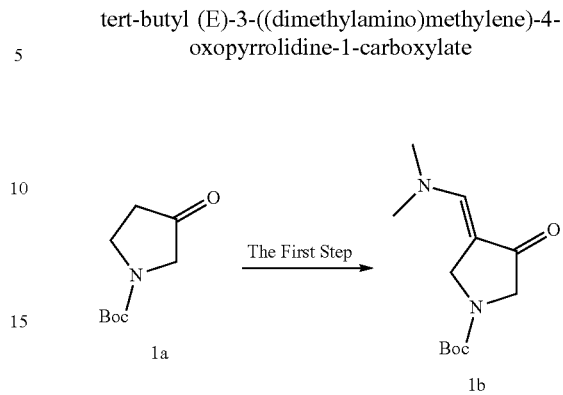

1a (500 g, 2.7 mol) was dissolved in N,N-dimethylformamide dimethyl acetal (3.5 L), and stirred under reflux for 5 hours, LCMS monitored the reaction to be completed. The temperature of reaction solution was lowered to room temperature, and the solvent was spin-dried. The residue was added with cyclohexane (500 mL), slurried, suction filtered, the solid was washed with cyclohexane (1 L*3), and dried under vacuum at 40° C. for 4 hours to obtain 1b (444 g, yellow solid, yield 69%). $^1$H NMR (400 MHz, CDCl 3) δ 7.31 (s, 1H), 4.57 (s, 2H), 3.81 (s, 2H), 3.09 (s, 6H), 1.48 (s, 9H). MS m/z (ESI): 241.3 [M+H].

The Second Step tert-butyl 6a-hydroxy-3a,4,6,6a-tetrahydropyrrole[3,4-c] pyrazole-5(1H)-carboxylate

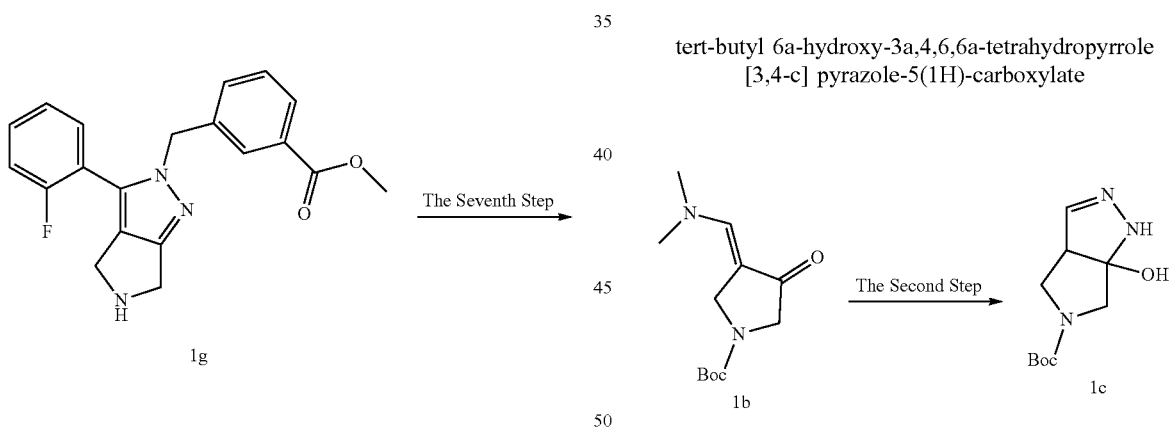

A toluene solution (50 mL) of 1b (10 g, 41.61 mmol) was carefully added with hydrazine hydrate (2.4 mL) dropwise. After dripping, the reaction flask was placed in a 45° C. oil bath for 16 hours. LCMS showed that the reaction was completed, and after the temperature of the reaction solution was returned to room temperature, a large amount of solids precipitated. After suction filtration, the solid was washed with cyclohexane (40 mL*3), and dried under vacuum at 40° C. for 1 hour to obtain 1c (8.2 g, pale yellow solid, yield 87%). $^1$H NMR (400 MHz, CDCl 3) δ 6.77 (s, 1H), 6.05 (br, 1H), 3.96-3.67 (m, 2H), 3.57 (d, J=11.7 Hz, 1H), 3.45-3.40 (m, 1H), 3.37-3.27 (m, 1H), 1.44 (s, 9H). MS m/z (ESI): 228.3 [M+H].

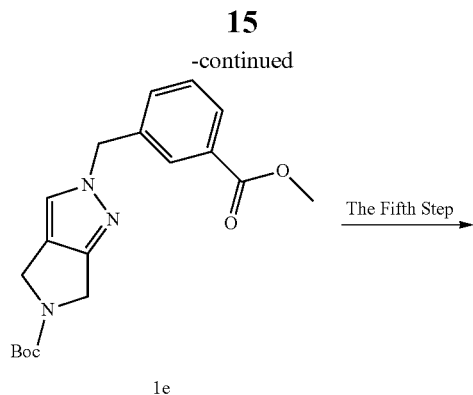

1e

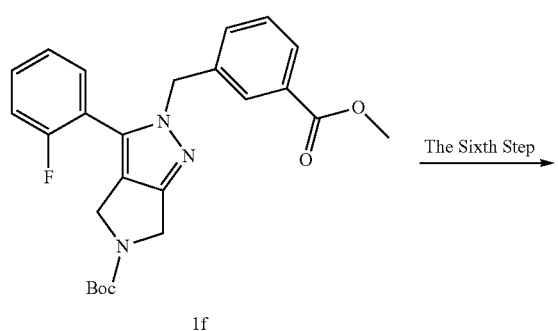

1f

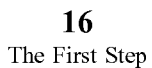

1g

1

The Third Step

2,6-dihydropyrrole [3,4-c]pyrazole-5(4H)-carboxylic acid tert-butyl ester

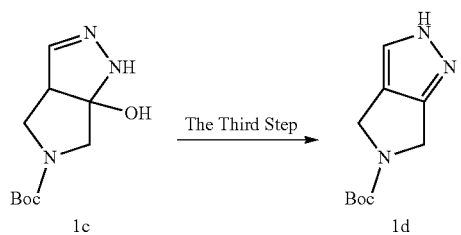 [SMILES: CC(C)(C)OC(=O)N1CC2C=NNC2(O)C1 ; CC(C)(C)OC(=O)N1Cc2c[nH]nc2C1]

Under an ice bath, a methanol solution (10 mL) of p-toluenesulfonic acid (0.646 g) was carefully added dropwise into a dichloromethane solution (100 mL) of 1c (8.2 g, 36.08 mmol). After dripping, it was naturally warmed to room temperature and stirred overnight. LCMS showed that the reaction was complete. 5% sodium bicarbonate aqueous solution (100 mL) was carefully added into the reaction solution. After stirred for 30 minutes, the mixture was left to stand still to separate the layers, and then the organic phase was washed with saturated brine (100 mL*2), dried with anhydrous sodium sulfate, filtered, and concentrated. Dichloromethane (5 mL) was added into the obtained residue, and cyclohexane (600 mL) was slowly added with stirring. At this time, a large amount of solids were gradually precipitated, suction filtered, the solids were washed with cyclohexane (40 mL*3), and dried under vacuum at 40° C. In 1 hour, 1d (5.3 g, yellow solid, yield 71%) was obtained. 1H NMR (400 MHz, CDCl 3) δ 10.41 (s, 1H), 7.32 (s, 1H), 4.49 (s, 4H), 1.52 (s, 9H). MS m/z (ESI): 210.2 [M+H].

The Fourth Step

2-(3-methoxycarbonyl)benzyl)-2,6-dihydropyrrole [3,4-c]pyrazole-5(4H)-carboxylic acid tert-butyl ester

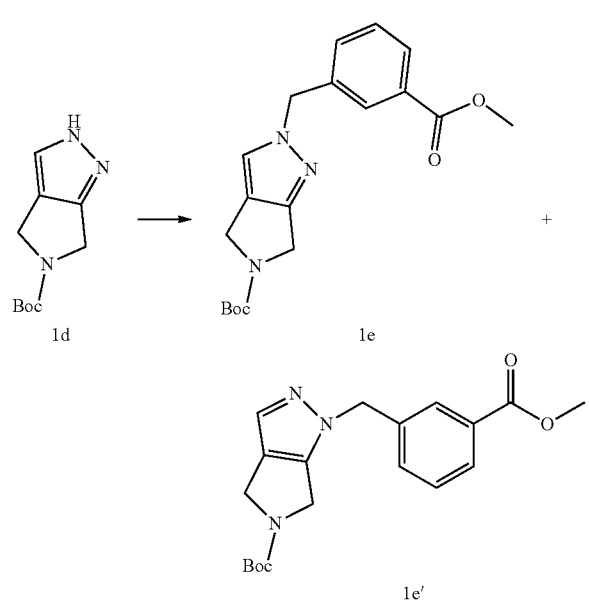

1d (4.5 g, 21.5 mmol) was dissolved in acetonitrile (150 mL), methyl 3-bromomethylbenzoate (5.9 g, 25.8 mmol) and cesium carbonate (21.1 g, 64.6 mmol) were added in turn, and the mixture was purged with the argon for 3 times, and placed in an 80° C. oil bath for reaction for 4 hours. After the reaction, the reaction solution was cooled, filtered, and the filtrate was concentrated to obtain a mixture of 1e and 1e' (8.7 g, yellow oil, yield 113%). MS m/z (ESI): 358.2 [M+H].

The Fifth Step

3-(2-fluorophenyl)-2-(3-(methoxycarbonyl)benzyl)-2,6-dihydropyrrolo[3,4-c]pyrazole-5(4H)-tert-butyl carboxylate

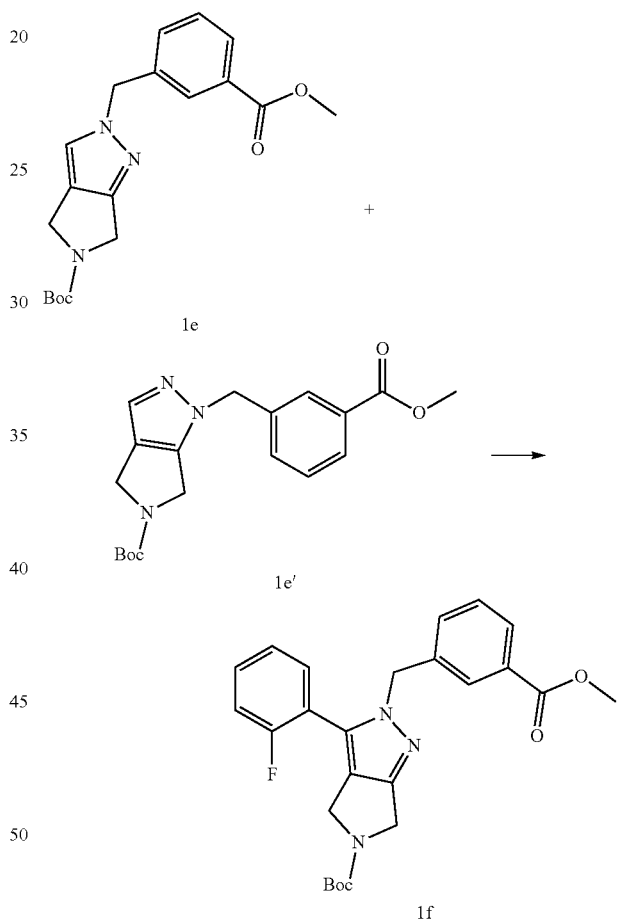

The mixture of 1e, 1e' (7.7 g, 21.6 mmol), o-fluoroiodobenzene (9.6 g, 43.1 mmol), potassium acetate (12.7 g, 129 mmol), allyl palladium chloride (II) dimer (785 mg, 2.16 mmol) and N,N-dimethylacetamide (100 mL) were added into the 250 ml round bottom flask in turns, the mixture was purged with argon for three times, and placed in an oil bath that was heated to 100° C. in advance for reaction overnight. The reaction solution was cooled, poured into water (150 mL), and then extracted with ethyl acetate (200 mL*3). The organic phase was combined and washed with saturated brine (150 mL*2), then dried over anhydrous sodium sulfate, filtered and concentrated. The residue was purified by column chromatography (petroleum ether: ethyl acetate=4:1) to obtain 1f (2.2 g, yellow oil, yield 23%). MS m/z (ESI): 452.2 [M+H].

The Step 6:

methyl 3-((3-(2-fluorophenyl)-5,6-dihydropyrrole[3,4-c]pyrazole-2(4H)-yl)methyl)benzoate 1f 1g 1f (2.2 g, 4.88 mmol), dichloromethane solution (24 mL) and trifluoroacetic acid (8 mL) were added into a 100 mL round bottom flask in sequence for reaction at room temperature overnight. After the reaction was completed, the reaction solution was concentrated to obtain 1 g (2.0 g, yellow oil, yield 100%), and the crude product was used in the next reaction. MS m/z (ESI): 352.2 [M+H].

The Seventh Step 3-((3-(2-fluorophenyl)-5-methyl-5,6-dihydropyrrolo[3,4-c]pyrazole-2(4H)-yl)methyl) methyl benzoate 1g

1

1 g (260 mg, 0.74 mmol) was taken in a 25 mL round bottom flask, a mixed solution of dichloromethane/methanol (2:1, 6 mL) was added, after it was stirred to dissolve, formaldehyde (37% in H2O, 300 mg, 3.70 mmol) was added. After stirred at room temperature for 30 minutes, sodium acetate borohydride (785 mg, 3.70 mmol) was added, and stirred for reaction at room temperature overnight. After the reaction was completed, compound 1 (yellow oil, 110 mg, 40.7%) was prepared. 1H NMR (400 MHz, CDCl δ 7.89 (d, J=7.7 Hz, 1H), 7.72 (s, 1H), 7.36 (m, 2H), 7.23-7.09 (m, 4H), 5.27 (s, 2H)), 3.88 (s, 3H), 3.85 (s, 2H), 3.75 (s, 2H), 2.64 (s, 3H). MS m/z (ESI): 366.2 [M+H].

Example 2

3-((3-(2-fluorophenyl)-5-methyl-5,6-dihydropyrrolo[3,4-c] pyrazole-2(4H)-yl)methyl)butyl benzoate

1

The First Step combined and washed with saturated brine (20 mL*3), then dried with anhydrous sodium sulfate, filtered and concentrated to obtain 2a (1.7 g, brown oil, yield 88%), MS m/z (ESI): 352.1[M+H].

The Second Step 3-((3-(2-fluorophenyl)-5-methyl-5,6-dihydropyrrolo[3,4-c]pyrazole-2(4H)-yl)methyl)butyl benzoate

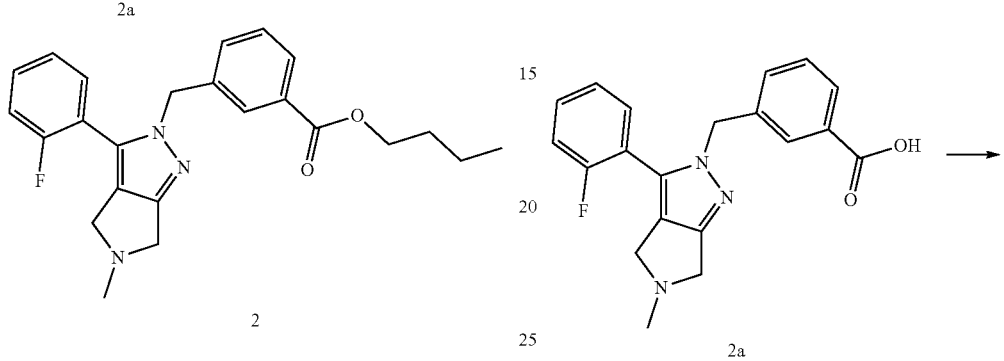

The First Step 3-((3-(2-fluorophenyl)-5-methyl-5,6-dihydropyrrole[3,4-c]pyrazole-2(4H)-yl)methyl) benzoic acid

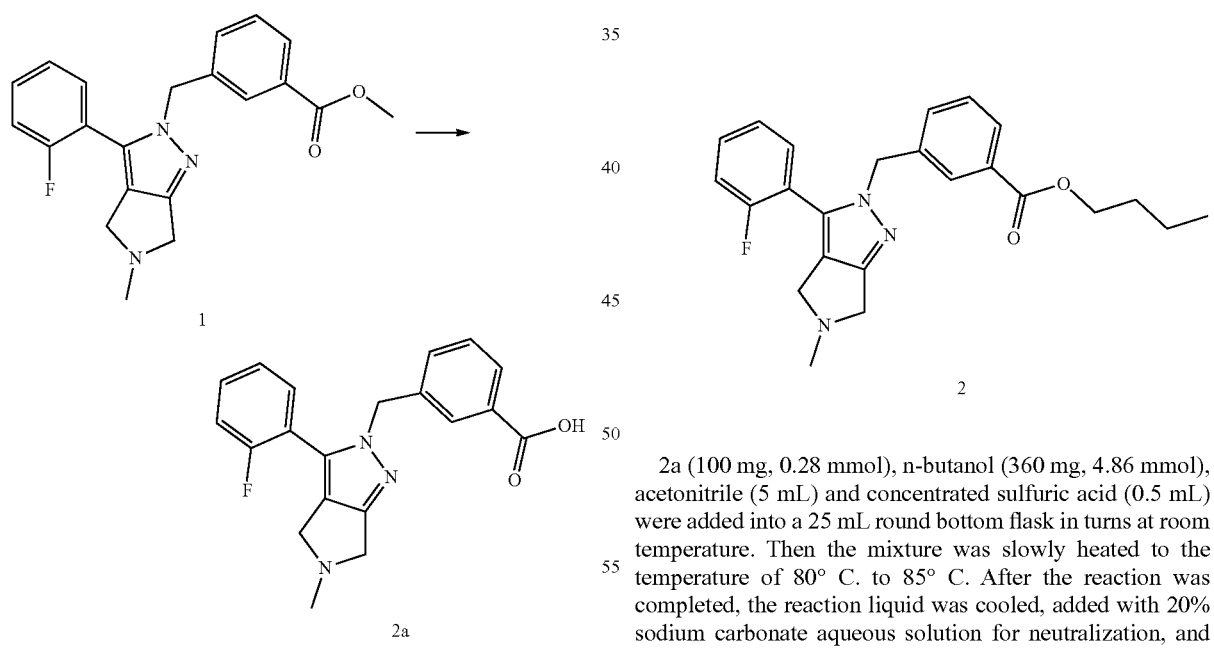

1 (2.0 g, 5.48 mmol), lithium hydroxide aqueous solution (2M, 11.4 mL, 22.8 mmol), tetrahydrofuran solution (60 mL) and water (15 mL) were added in a 100 mL round bottom flask in sequence, and stirred for reaction at room temperature for 3 hours. After the reaction was completed, the reaction solution was added with dilute hydrochloric acid (1N) to adjust the pH to weak acidity, and then extracted with dichloromethane (50 mL*3). The organic phases were 2a (100 mg, 0.28 mmol), n-butanol (360 mg, 4.86 mmol), acetonitrile (5 mL) and concentrated sulfuric acid (0.5 mL) were added into a 25 mL round bottom flask in turns at room temperature. Then the mixture was slowly heated to the temperature of 80° C. to 85° C. After the reaction was completed, the reaction liquid was cooled, added with 20% sodium carbonate aqueous solution for neutralization, and extracted with dichloromethane. The organic phases were combined and washed with water, dried over sodium sulfate, filtered, and concentrated. The residue was purified by a silica gel column to obtain compound 2 (62 mg, colorless oil, 54%). MS m/z (ESI): 408.2 [M+H]. 1H NMR (400 MHz, CDCl3) δ 7.88 (d, J=7.6 Hz, 1H), 7.67 (s, 1H), 7.36 (m, 2H), 7.23-7.09 (m, 4H), 5.25 (s, 2H)), 4.21 (q, J=7.2 Hz, 3H), 3.81 (s, 2H), 3.76 (s, 2H), 2.68 (s, 3H), 1.82 (m, 2H), 1.49 (m, 2H), 0.88 (t, J=6.8 Hz, 3H).

Example 3

3-((3-(2-fluorophenyl)-5-methyl-5,6-dihydropyrrolo[3,4-c] pyrazole-2(4H)-yl)methyl) ethyl benzoate

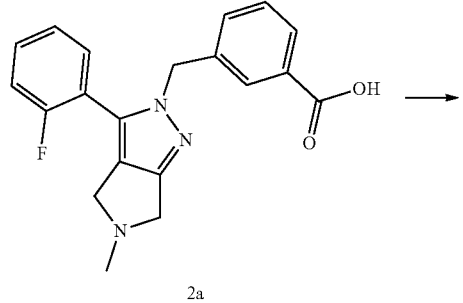

2a

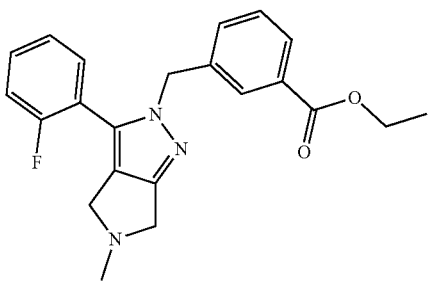

3

2a (100 mg, 0.28 mmol), ethanol (5 mL) and concentrated sulfuric acid (0.5 mL) were added into a 25 mL round bottom flask at room temperature. Then the mixture was slowly heated to the temperature of 80 to 85° C. After the completion of the reaction, the reaction liquid was cooled, added with 20% sodium carbonate aqueous solution for neutralization, and extracted with dichloromethane. The organic phases were combined and washed with water, dried over sodium sulfate, filtered, and concentrated. The residue was purified by a silica gel column to obtain compound 3 (87 mg, colorless oil, 82%). MS m/z (ESI): 380.2 [M+H]. 1H NMR (400 MHz, CDCl$_3$) δ 7.90 (d, J=7.6 Hz, 1H), 7.75 (s, 1H), 7.40-7.36 (m, 2H), 7.24-7.08 (m, 4H), 5.35 (s, 2H), 4.15 (q, J=7.2 Hz, 3H), 3.84 (s, 2H), 3.72 (s, 2H), 2.65 (s, 3H), 1.31 (t, J=7.2 Hz, 3H).

Example 4

N-cyclopropyl-3-((3-(2-fluorophenyl)-5-methyl-5,6-dihydropyrrolo[3,4-c]pyrazole-2(4H)-Yl)methyl) benzamide

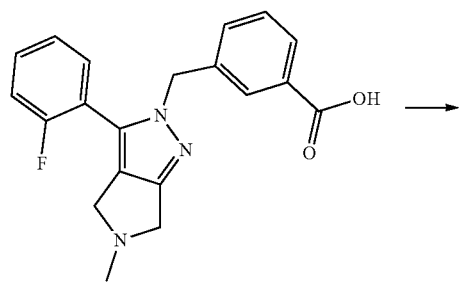

2a

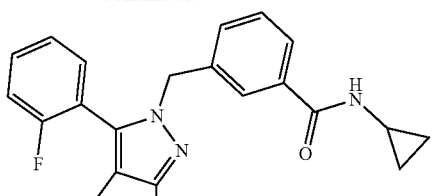

4

Cyclopropylamine (1 mL) was added into the mixed solution of 2a (50 mg, 0.142 mmol), HATU (82 mg, 0.214 mmol) and DMF (2 mL) for reaction at room temperature overnight. LCMS detected that compound 4 (12.2 mg, white solid, yield: 22.0%) was directly prepared after the reaction was completed. MS m/z (ESI): 391.3[M+1]; 1H NMR (400 MHz, CDCl3) δ 7.60 (d, J=7.7 Hz, 1H), 7.45-7.35 (m, 2H), 7.29 (dd, J=13.1, 5.4 Hz, 1H), 7.16 (ddd, J=21.7, 15.7, 7.7 Hz, 4H), 6.14 (s, 1H), 5.25 (s, 2H), 3.85 (s, 2H), 3.75 (s, 2H), 2.97-2.79 (m, 1H), 2.68 (s, 3H), 0.86 (q, J=6.8 Hz, 2H), 0.60 (t, J=7.9 Hz, 2H).

Example 5

1-amino-2-methyl-1-oxopropan-2-yl-3-((3-(2-fluorophenyl)-5-methyl-5,6-dihydropyrrolo [3,4-c]pyrazole-2(4H)-yl)methyl)benzoate

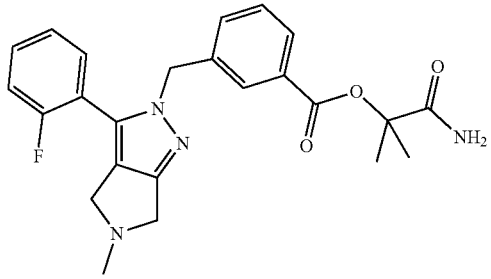

2a

-continued

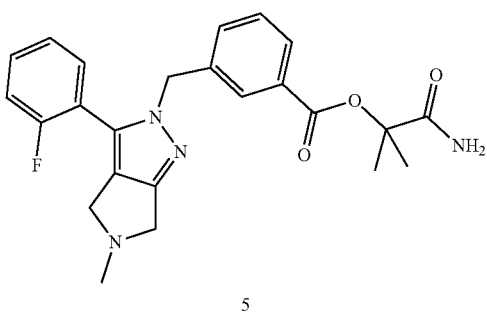

5

2a (150 mg, 0.427 mmol), 2-bromoisobutyramide (36 mg, 0.214 mmol), silver oxide (198 mg, 0.854 mL), acetonitrile (2 mL) and water (0.1 mL) were added into a 25 mL round bottom flask in turn, and the mixture was stirred at room temperature. After the reaction, the reaction solution was concentrated, filtered and concentrated. The residue was prepared by HPLC (acetonitrile/water (containing 0.05% trifluoroacetic acid) gradient washing) to obtain compound 5 (trifluoroacetate, salt coefficient=3.0, salt molecular weight: 778.17, 18.4 mg, colorless oil). $^1$H NMR (400 MHz, MeOD) δ 7.90 (d, J=8.0 Hz, 1H), 7.65 (s, 1H), 7.57-7.53 (m, 1H), 7.43-7.25 (m, 5H), 5.41 (s, 2H), 4.70-4.52 (m, 4H), 3.18 (s, 3H), 1.67 (s, 6H). MS m/z (ESI): 437.4 [M+H].

Example 6

3-((5-methyl-3-(o-tolyl)-5,6-dihydropyrrolo[3,4-c]pyrazole-2(4H)-yl)methyl) Methyl benzoate

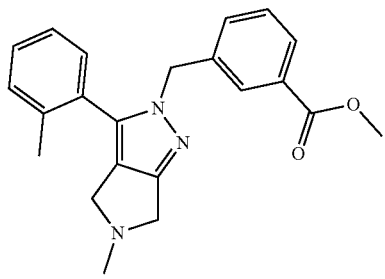

-continued

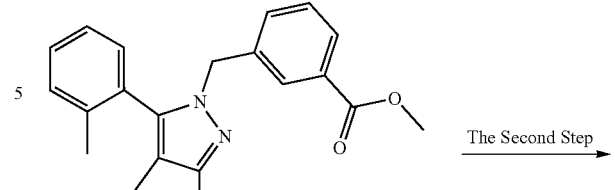

The Second Step →

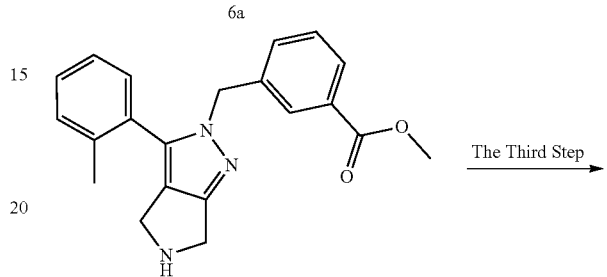

The Third Step →

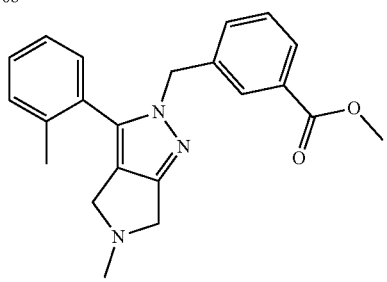

The First Step 2-(3-(methoxycarbonyl)benzyl)-3-(o-tolyl)-4,6-dihydropyrrole [3,4-c]pyrazole-5(2H)-carboxy Tert-butyl ester 1e (770 mg, 2.16 mmol), 2-iodotoluene (0.96 g, 4.31 mmol), potassium acetate (1.27 g, 12.9 mmol), and allylpalladium(II) chloride dimer and N,N-dimethylacetamide (10 mL) were added in a 50 mL round bottom flask in turn (78.5 mg, 0.216 mmol), the mixture was purged with argon for three times, and placed in an oil bath that was raised to 100° C. in advance for reaction overnight. The reaction solution was cooled, poured into water (30 mL), and then extracted with ethyl acetate (25 mL*3). The organic phases were combined and washed with saturated brine (15 mL*2), then dried over anhydrous sodium sulfate, filtered and concentrated. The residue was purified by column chromatography (petroleum ether: ethyl acetate=4:1) to obtain 6a (299 mg, yellow oil, yield 31%). MS m/z (ESI): 448.2 [M+H].

The Second Step 3-((3-(o-tolyl)-5,6-dihydropyrrole[3,4-c]pyrazole-2(4H)-yl)methyl) methyl benzoate 6a (299 mg, 0.67 mmol), dichloromethane solution (10 mL) and trifluoroacetic acid (5 mL) were added into the 25 mL round bottom flask for reaction at room temperature overnight. After the reaction was completed, the reaction solution was concentrated to obtain 6b (232 mg, yellow oil, yield 100%), and the crude product was used in the next reaction. MS m/z (ESI): 348.2 [M+H].

The Third Step 3-((5-methyl-3-(o-tolyl)-5,6-dihydropyrrolo[3,4-c]pyrazole-2(4H)-yl) methyl) methyl benzoate 6b (232 mg, 0.65 mmol), aqueous formaldehyde solution (37%, 429 mg, 5.28 mmol), dichloromethane (6 mL) and methanol (3 mL) were added into a 25 mL round bottom flask in sequence and stirred for reaction at room temperature for 30 minutes, acetic acid borohydride Sodium (1.11 g, 5.28 mmol) was added, and continued to be stirred overnight. After the reaction was completed, the reaction solution was concentrated and purified by column chromatography to obtain 6 (156 mg, colorless oil, yield 66%). MS m/z (ESI): 366.1 [M+H]. $^1$H NMR (400 MHz, CDCl3) δ 7.86 (d, J=7.6 Hz, 1H), 7.71 (s, 1H), 7.50-7.40 (m, 2H), 7.32-7.15 (m, 4H), 5.22 (s, 2H), 3.86 (s, 3H), 3.82 (s, 2H), 3.72 (s, 2H), 2.62 (s, 3H), 2, 51 (s, 3H).

Example 7

2-Fluoro-5-((5-methyl-3-(o-tolyl)-5,6-dihydropyrrole [3,4-c]pyrazole-2 (4H)-yl) methane Yl) methyl benzoate

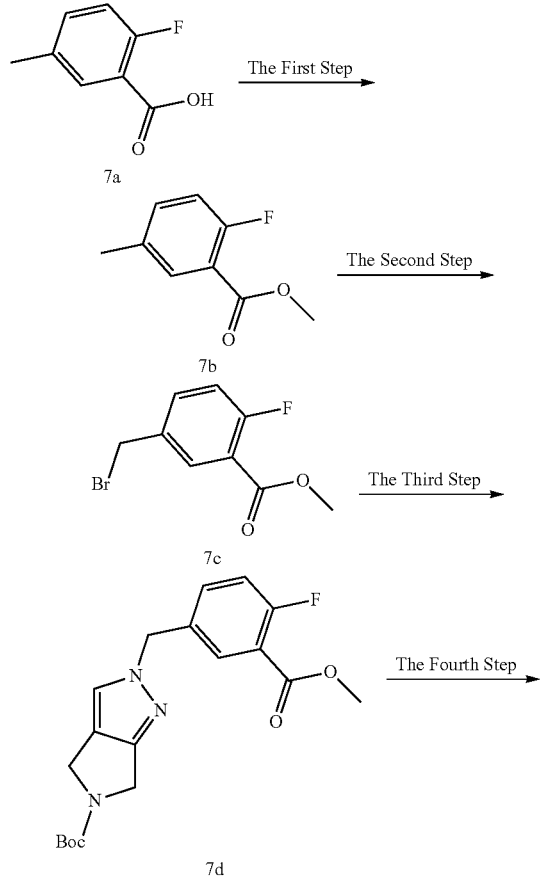

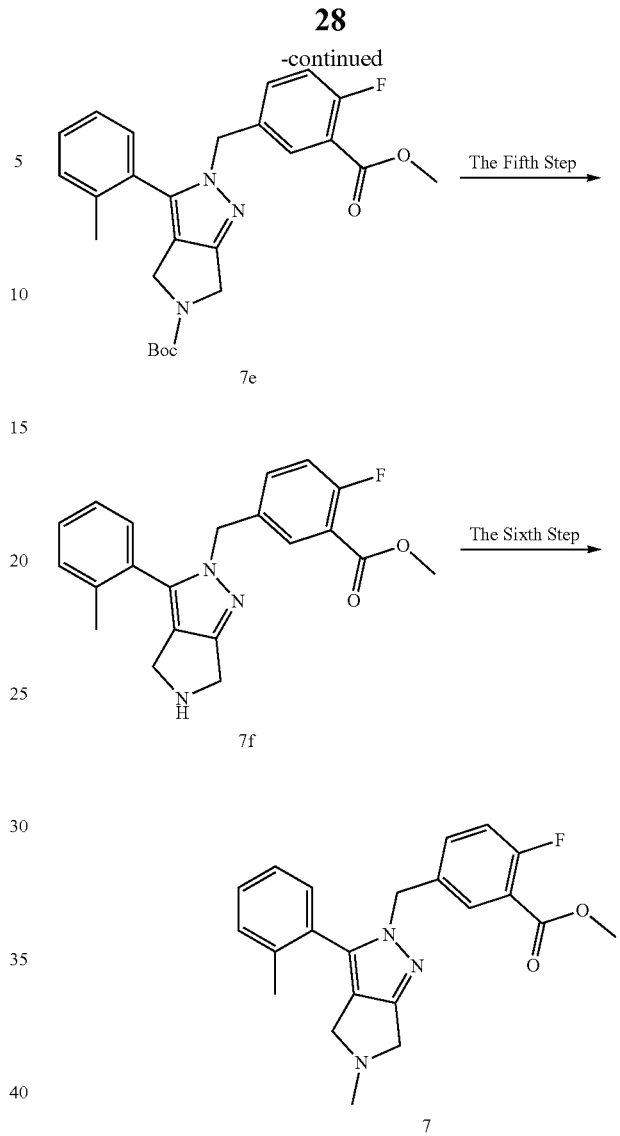

The first step 1: 2-fluoro-5-methyl methyl benzoate

Thionyl chloride (5 mL) was added into 7a (5 g, 32.47 mmol) in methanol (120 mL) for reaction at 50° C. for 2 hours. After the completion of the reaction was detected by LCMS, the reaction solution was concentrated, diluted with ethyl acetate (150 mL), and washed with saturated sodium bicarbonate aqueous solution (50 mL*3). The organic phases were combined, washed with saturated brine (50 mL*2), dried over anhydrous sodium sulfate, and concentrated to obtain 7b (5.1 g, light yellow oil, 93%). MS m/z (ESI): 169.1 [M+1].

The second step: 5-bromomethyl-2-fluorobenzoic acid methyl ester Carbon tetrachloride (36 mL) was added into the mixture of N-bromosuccinimide (2.12 g, 11.90 mmol), 7b (2 g, 11.90 mmol) and azobisisobutyronitrile (976 mg, 5.95 mmol). The oil pump was used to purge for four times and the mixture was heated in an 80° C. oil bath for 6 hours. After the completion of the reaction was detected by LCMS, the reaction solution was cooled to room temperature, and the concentrated residue was column chromatographed to obtain 7c (1.5 g, light yellow solid, yield 48%). MS m/z (ESI): 226.1 [M-20].

The Third Step 2-(4-fluoro-3-(methoxycarbonyl)benzyl)-4,6-dihydropyrrole [3,4-c] pyrazole-5(2H)-carboxylic acid tert-butyl ester Acetonitrile (30 mL) was added into a mixture of 1d (927 mg, 4.44 mmol), 7c (1.2 g, 4.88 mmol) and cesium carbonate (2.891.30 g, 8.88 mmol) for reaction at 80° C. for one hour. After the reaction was detected by LCMS, the reaction solution was filtered, and the filtrate was concentrated and separated by column chromatography (petroleum ether/ethyl acetate=6/1) to obtain a mixture of 7d and 7d' (positional isomers) (1.3 g, white solid, Yield: 78%). MS m/z (ESI): 376.2 [M+1].

The Fourth Step 2-(4-fluoro-3-(methoxycarbonyl)benzyl)-3-(o-tolyl)-4,6-dihydropyrrole

[3,4-c]pyrazole-5(2H)-tert-butyl carboxylate the mixture of 7d and 7d' (1.3 g, 3.47 mmol), potassium acetate (2.04 g, 20.82 mmol), allylpalladium(II) chloride dimer (127 mg, 0.35 mmol), O-methyl iodobenzene (1.5 g, 6.94 mmol) and N,N-dimethylacetamide (40 mL) were added into a 100 mL round bottom flask in turn. After the mixture was purged for four times with an oil pump, the mixture was put into an oil bath which was raised to 100° C. in advance for reaction overnight. After the reaction was cooled to room temperature, the reaction solution was poured into water (100 mL), and then extracted with ethyl acetate (100 mL*3). The organic phase was combined, washed with saturated brine (50 mL*2), and dried with anhydrous sodium sulfate. The concentrated residue was purified by column chromatography to obtain 7e (320 mg, pale yellow oil, yield 20%). MS m/z (ESI): 466.3 [M+1].

The Fifth Step 2-fluoro-5-((3-(o-tolyl)-5,6-dihydropyrrolo[3,4-c] pyrazole-2(4H)-yl) methyl) benzene methyl formate Trifluoroacetic acid (1 mL) was added into a solution of 7e (510 mg, 1.10 mmol) in dichloromethane (3 mL) for reaction at room temperature for 2 hours. After LCMS detected the reaction was completed, the mixture was directly concentrated to obtain the crude product of 7f (450 mg, the crude product of black oil). MS m/z (ESI): 366.3 [M+1].

The Sixth Step 2-fluoro-5-((5-methyl-3-(o-tolyl)-5,6-dihydropyrrole [3,4-c] pyrazole-2(4H)-yl) methane Yl) methyl benzoate A 37% aqueous formaldehyde solution (0.8 mL) was added into a dichloromethane (4 mL)/methanol (2 mL) mixed solution of 7f (450 mg, 1.23 mmol), and the mixture was stirred at room temperature for 1 hour. Sodium acetate borohydride (1.56 g, 7.38 mmol) was added into the above reaction solution. After reacting at room temperature for 16 hours, the reaction solution was concentrated, and the residue was prepared by high pressure liquid chromatography (acetonitrile/water (containing 0.05% trifluoroacetic acid) gradient washing) to obtain compound 7 (trifluoroacetate, salt coefficient=2.3, 33.0 mg) Colorless oil, yield: 4.2%). $^1$H NMR (400 MHz, CDCl3) δ 7.55-7.36 (m, 3H), 7.23-7.14 (m, 3H), 7.08 (s, 1H), 7.03-7.01 (m, 1H), 5.27 (s, 2H), 3.91 (d, 4H), 3.08 (s, 3H), 2.89 (s, 3H), 2.75 (s, 3H). MS m/z (ESI): 380.2 [M+1].

Example 8

3-((5-Methyl-3-(o-tolyl)-5,6-dihydropyrrolo[3,4-c] pyrazole-2(4H)-yl) methyl) benzene Tert-butyl formate

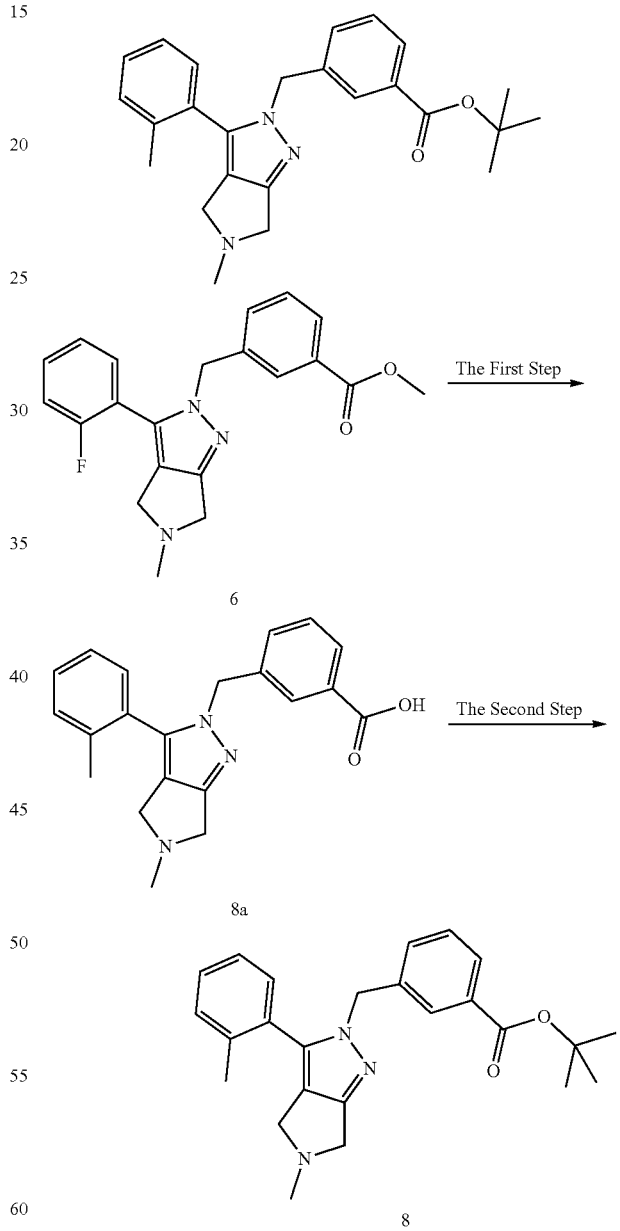

The First Step 3-((5-methyl-3-(o-tolyl)-5,6-dihydropyrrole [3,4-c] pyrazole-2(4H)-yl) methyl) benzene formic acid 6 (100 mg, 0.28 mmol), aqueous lithium hydroxide solution (2M, 1.2 mL, 2.28 mmol), tetrahydrofuran solution (2 mL) and water (0.5 mL) were sequentially added into a 10 mL round bottom flask, and stirred at room temperature for 3 hours. After the reaction, the reaction solution was added with dilute hydrochloric acid (1N) to adjust the pH to weak acidity, and then extracted with dichloromethane (5 mL*3). The organic phases were combined and washed with saturated brine (5 mL*3), then dried with anhydrous sodium sulfate, filtered and concentrated to obtain 8a (88 mg, pale yellow oil, yield 92%), MS m/z (ESI): 348.1[M+H].

The Second Step 3-((5-methyl-3-(o-tolyl)-5,6-dihydropyrrolo[3,4-c] pyrazole-2(4H)-yl) methyl) benzene tert-butyl formate 4-Dimethylaminopyridine (15 mg, 0.125 mmol) was dissolved in 3 mL of tert-butanol, and compound 8a (88 mg, 0.25 mmol) and tert-butyl carbonate (109 mg, 0.5 mmol) were added into the solution in turn. The reaction mixture was stirred at 20 degrees for 12 hours. The reaction solution was concentrated and purified by column chromatography to obtain 8 (36 mg, pale yellow oil, yield 36%). MS m/z (ESI): 404.2 [M+H]. 1H NMR (400 MHz, CDCl 3) 67.91 (d, J=7.6 Hz, 1H), 7.73 (s, 1H), 7.50-7.40 (m, 2H), 7.32-7.15 (m, 4H), 5.24 (s, 2H), 3.84 (s, 2H), 3.75 (s, 2H), 2.64 (s, 3H), 2, 51 (s, 3H), 1.38 (s, 9H).

Example 9

3-((3-(2,4-Difluorophenyl)-5-methyl-5,6-dihydropyrrolo [3,4-c] pyrazole-2(4H)-yl) Methyl) methyl benzoate

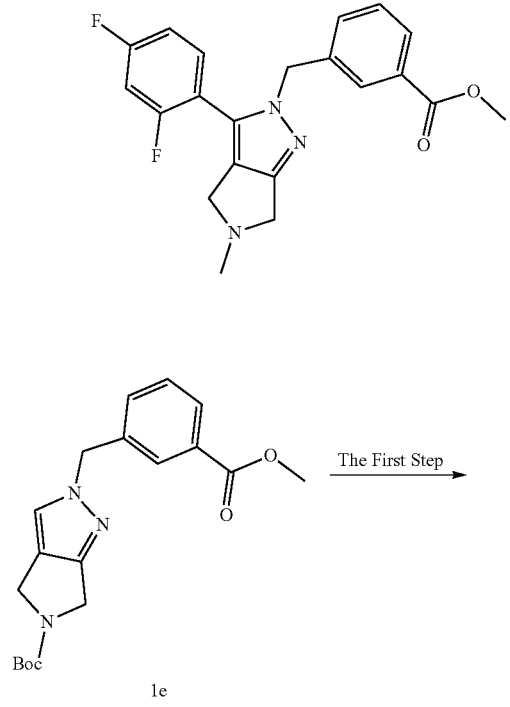

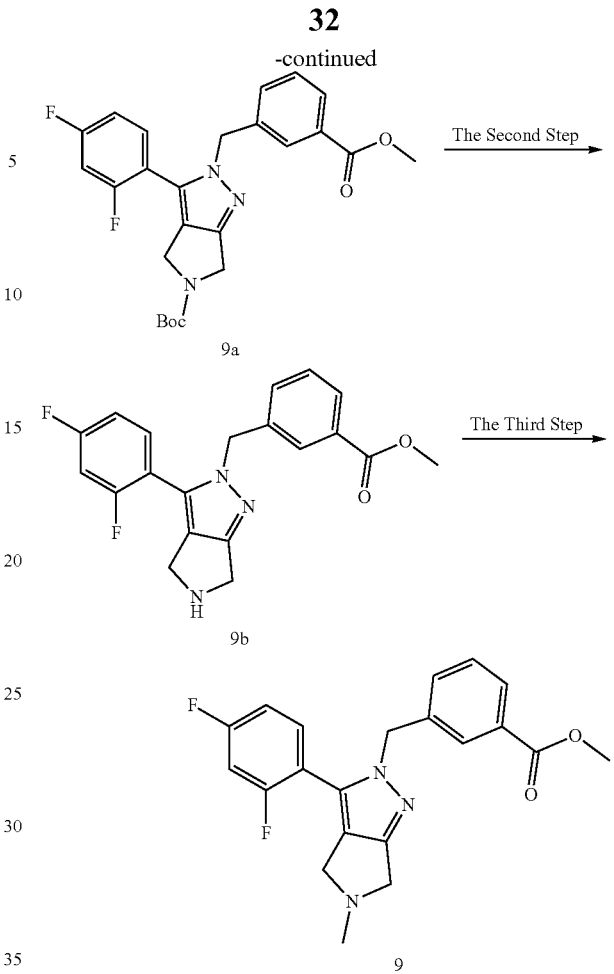

The First Step 3-(2,4-difluorophenyl)-2-(3-(methoxycarbonyl)benzyl)-4,6-dihydropyrrole [3,4-c] pyrazole-5 (2H)-carboxylic acid tert-butyl ester 1e (1.0 g, 2.80 mmol) and potassium acetate (1.65 g, 16.8 mmol) were added in a 100 mL three-hole round bottom bottle, a stir bar was put into it, and allyl palladium chloride (102 mg, 0.28 mmol) was added, then purged. Under the protection of argon, 2,4-difluoroiodobenzene (1.34 g, 5.6 mmol) was added in DMA (50 mL) solution, pump argon, and stirred for 2 hours in a 100° C. oil bath. LCMS monitored the end of the reaction. The reaction solution was added with 100 mL of water, and the mixture was extracted with ethyl acetate (50 mL×3), the organic phases were combined and washed with water (20 mL×3), dried over anhydrous sodium sulfate, filtered and spin-dried, then used PE, PE/EA=20:1,10:1,5:1 (petroleum ether/ethyl acetate=2:1, R f=0.5) column fraction to obtain the target product 9a (156 mg, yellow solid, yield: 11.5%), MS m/z (ESI): 470.3 [M+1].

The Second Step 3-((3-(2,4-difluorophenyl)-5,6-dihydropyrrolo[3,4-c] pyrazole-2(4H)-yl) methyl) benzene Methyl formate 9a (156 mg, 0.333 mmol) was added into a 50 mL round bottom flask, and a mixed solution of dichloromethane/ trifluoroacetic acid (3:1, 4 mL) was added for reaction at room temperature for 1 hour. LCMS monitored the end of the reaction, and the reaction solution was spin-dried to obtain the crude product 9b (110 mg), which was directly reacted further. MS m/z (ESI): 370.3 [M+1].

The Third Step 3-((3-(2,4-difluorophenyl)-5-methyl-5,6-dihydropyr-rolo

[3,4-c]pyrazole-2(4H)-yl)Methyl)methyl benzoate 9b (123 mg, 0.33 mmol, containing trifluoroacetic acid) was added into a 100 mL round bottom flask, and a mixed solution of dichloromethane/methanol (2:1, 6 mL) was added, and the mixture was stirred to dissolve, formaldehyde (37% in $H_2O$, 216 mg, 2.67 mmol) was added, after stirred at room temperature for 40 minutes, sodium acetate borohydride (565 mg, 2.67 mmol) was added, and was stirred at room temperature for reaction for 2 hours. The reaction was monitored by LCMS. Ammonia was added dropwise to the reaction solution. After adjusting the pH to alkaline, the mixture was extracted with dichloromethane (5 mL×3). The organic phase was washed with saturated brine, dried over anhydrous sodium sulfate, filtered and spin-dried to obtain 143 mg. The crude product was prepared and further purified to obtain the target product 9 (80 mg, yellow oil, two-step yield: 63%) 1H NMR (400 MHz, CDCl 3) δ 7.90 (d, J=7.8 Hz, 1H), 7.69 (s, 1H), 7.33 (t, J=7.7 Hz, 1H), 7.15 (m, 2H), 6.90 (m, 2H), 5.24 (s, 2H), 3.88 (d, J=6.7 Hz, 3H), 3.84 (s, 2H), 3.72 (s, 2H), 2.63 (s, 3H). MS m/z (ESI): 384.2 [M+1].

Test example: determination of compounds' inhibition of $H^+/K^+$ATPase enzyme activity The following experiment is used to determine the inhibitory effect of the compound of the present invention on the $H^+/K^+$ATPase enzyme activity.

1. Experimental materials

Plate reader: SpectraMax M5 (MD)
Malachite Green (Sigma Aldrich, 213020-25G)
Ammonium molybdate (Sigma Aldrich, 277908-20G)
ATP (Sigma Aldrich, A1852-1VL).

2. Buffer preparation

Enzyme working solution: titrating the enzyme, diluting the enzyme with buffer 1, and during the reaction, taking 5 μl of the diluted solution into 50 μl reaction system.
ATP solution: 100 mM ATP was diluted to 5 mM with no K+buffer, and 5 μl of the diluted solution was added to the 50 μl reaction system, that is, the final concentration of ATP was 500 μM.
MLG color development liquid: 0.12% MLG, 7.5% ammonium molybdate, and 110% Tween-20 was mixed as 100: 25:2, and adding 15 μl of the mixture into each well during detection.
Buffer 1: 50 mM Tris-HCl pH 6.5, 5 mM magnesium chloride (magnesium chloride), 10 μM valinomycin (valinomycin).
Buffer 2: 50 mM Tris-HCl pH 6.5, 5 mM magnesium chloride (magnesium chloride), 10 μM valinomycin (valinomycin), 20 mM KCl.
Homogenization buffer: 10 mmol/L Tris-HCl, pH 6.8, 0.25M sucrose (sucrose), 1 mmol/LEDTA. 7.5% Ficoll layering solution: homogenization buffer+7.5% (W/W) 400 (Ficoll 400).

3. Experimental steps 3.1. $H^+/K^+$ ATPase enzyme extraction (1) The stomach tissue of the rabbit was separated, and the blood was washed with tap water, food residue.

(2) The fundus portion was thoroughly washed with pre-cooled NaCl solution to remove surface mucus.

(3) The stripped mucosa was filled into a sample bag or a 50 ml centrifuge tube, and quickly freezing in a liquid nitrogen tank.

(4) The tissue was removed, minced with surgical scissors, and a pre-cooled homogenization buffer (4 ml/g tissue) was added and homogenized in a tissue homogenizer for 2 to 10 minutes.

(5) After homogenization, if there were larger tissue particles, they could be removed by centrifugation (600 g, 10 min), and then the supernatant was transferred to a clean centrifuge tube. After centrifugation at 20000 g for 30 minutes, then the supernatant was transferred to a clean centrifuge tube at 100000 g for 90 minutes and the precipitate was collected.

(6) Resuspending the precipitate with homogenization buffer, blowing uniformly, adding 7.5% Ficoll layering solution at equal ratio, centrifuging at 100000 g for 90 minutes, and collecting the precipitate.

(7) Resuspending the precipitate with homogenization buffer, blowing uniformly, and the protein concentration was measured by Bradford. Freezing in tubes at −80° C. for later use.

3.2. $H^+/K^+$ ATPase activity experiment (1) Adding 35 μl of reaction buffer to each experimental well, and then added 35 μl of buffer 1.

(2) Adding 5 μl buffer 1 containing 10% DMSO to the whole enzyme and buffer well.

(3) Adding 5 μl of 10× compound working solution to the compound well and mixing well.

(4) Adding 5 of buffer 1 to the buffer well.

(5) Adding 5 μl of 10× enzyme working solution to the remaining wells, mixing and incubating at 37° C. for 30 minutes.

(6) Adding 5 μl of 10XATP working solution to all experimental wells, and incubating at 37° C. for 20 min.

(7) Adding 15 μl MLG chromogenic solution to all experimental wells, and uniformly mixing and incubating at room temperature for 5-30 min.

(8) The reading number of 620 nm was detected by an M5 instrument.

4. Data analysis

The inhibition rate is calculated with the following formula:

Inhibition rate ($IC_{50}$)=[OD (sample well)−OD (full enzyme well containing potassium chloride)]/ [(OD (full enzyme well containing potassium chloride)−(OD (full enzyme well without potassium chloride Enzyme hole)]×100%

5. Experimental results

The inhibition rate ($IC_{50}$) of each example compound is shown in Table 2.

TABLE 2

| Compound number | $IC_{50}(\mu M)$ |
| --- | --- |
| Example 1 | 0.0776 |
| Example 2 | 0.0968 |
| Example 3 | 0.0904 |
| Example 4 | 0.5395 |
| Example 5 | 0.2248 |
| Example 6 | 0.03662 |
| Example 7 | 0.03895 |
| Example 8 | 0.5888 |
| Example 9 | 0.06139 |

As can be seen from Table 2, the compounds of the present invention have excellent $H^+/K^+$ ATPase enzyme inhibitory activity and can be used to prepare gastric acid secretion inhibitors.

The invention claimed is:

1. A compound represented by general formula (I) or a pharmaceutically acceptable salt thereof,

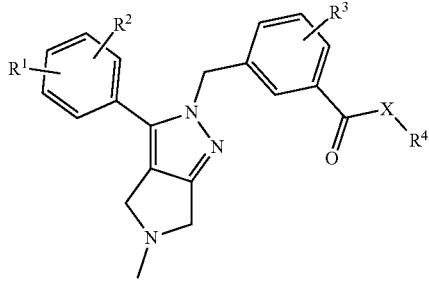

(I)

wherein:
X is O;
$R^1$ and $R^2$ are each independently selected from hydrogen atom or fluorine atom;
$R^3$ is hydrogen atom;
$R^4$ is selected from $C_{1-4}$ alkyl amide.

2. The compound or a pharmaceutically acceptable salt thereof of claim 1, wherein the compound is:
1-amino-2-methyl-1-oxoprop-2-yl-3-((3-(2-fluorophenyl)-5-methyl-5,6-dihydropyrrolo[3,4-c) pyrazole-2(4H)-yl) methyl) benzoate.

3. A pharmaceutical composition, comprising the compound or a pharmaceutically acceptable salt thereof of claim 1 and a pharmaceutically acceptable carrier, excipient, or diluent.

* * * * *